United States Patent [19]

Rohr et al.

[11] 4,127,463

[45] Nov. 28, 1978

[54] PROBE FOR AN ELECTROCHEMICAL OXYGEN MEASUREMENT PICKUP

[75] Inventors: Franz-Josef Rohr, Abtsteinach; Hubert Holick, Lampertheim, both of Germany

[73] Assignee: Brown, Boveri & Cie AG, Mannheim-Kafertal, Germany

[21] Appl. No.: 816,173

[22] Filed: Jul. 15, 1977

[30] Foreign Application Priority Data

Jul. 17, 1976 [DE] Fed. Rep. of Germany ....... 2632250

[51] Int. Cl.² .......................................... G01N 27/58
[52] U.S. Cl. ............................................... 204/195 S
[58] Field of Search ............. 204/195 S, 1 S; 324/29, 324/71 R; 60/276; 123/119 E

[56] References Cited

U.S. PATENT DOCUMENTS

| 3,909,385 | 9/1975 | Spielberg et al. | 204/195 S |
| 3,940,327 | 2/1976 | Wagner | 204/195 S |
| 3,978,006 | 8/1976 | Topp et al. | 204/195 S X |

Primary Examiner—G. L. Kaplan
Attorney, Agent, or Firm—Herbert L. Lerner

[57] ABSTRACT

A probe for an electrochemical oxygen measurement pickup having an oxygen ion-conducting solid electrolyte with electrodes and electrical contact points connected by conductors to the electrodes, in which the probe has an electrochemically active region provided with the electrodes and an electrochemically passive region provided with the contact points as well as with their electrical connections to the electrodes. This minimizes or avoids false readings resulting from temperature gradient and changes in chemical equilibrium.

5 Claims, 6 Drawing Figures

PROBE FOR AN ELECTROCHEMICAL OXYGEN MEASUREMENT PICKUP

BACKGROUND OF THE INVENTION

1. Field of the Invention

This invention relates to a probe for an electrochemical oxygen measurement pickup having a solid, oxygen ion-conducting electrolyte with electrodes, and contact points at the end, which are connected to the electrodes in an electron-conducting manner.

2. Description of the Prior Art

Probes (sensor elements) for oxygen measurement pickups often consist of an ion-conducting solid-electrolyte tube which is closed on one end and the inner and outer surfaces of which are provided with electrodes. These electrodes extend up to the open end of the solid-electrolyte tube and form there the electrical contact points, from which the electric probe voltage is taken and is conducted to external terminals. If such measuring pickups are used, there is danger of false measurements, as the solid-electrolyte tube which usually protrudes transversely into the hot gas stream has a temperature gradient from its tip to its end and therefore has different ion conductivity. As a result, a voltage which decreases from the probe tip toward the end is delivered and the resultant electric voltage which is taken off at the contact points is thereby inaccurate and cannot be related unequivocally to a definite oxygen content of the gas to be measured.

If, in addition, the electrode exposed to the gas to be measured must be catalytically effective and must bring the gas components into chemical equilibrium, then the chemical equilibrium is adjusted differently along the probe in accordance with the temperature gradient. From this, different gas concentrations result and therefore, different electric electrode voltages (mixed potentials), which additionally falsify the electrical signal of the probe.

SUMMARY OF THE INVENTION

An object of the invention is to provide a probe for oxygen measurement pickups of the type mentioned which will deliver a more accurate voltage measurement, i.e., a measurement substantially free of the errors resulting from temperature gradient and variances in chemical equilibrium.

With the foregoing and other objects in view, there is provided in accordance with the invention a probe for an electrochemical oxygen measurement pickup having an oxygen ion-conducting solid electrolyte with electrodes and electrical contact points connected to the electrodes, of an electrochemically active region of the probe which has the electrodes and the oxygen ion-conducting solid electrolyte for passage of oxygen ions through the solid electrolyte, and an electrochemically passive region of the probe which carries the contact points as well as their electrical connections to the electrodes.

Other features which are considered as characteristic for the invention are set forth in the appended claims.

Although the invention is illustrated and described herein as embodied in a probe for an electrochemical oxygen measurement pickup, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings, in which.

DETAILED DESCRIPTION OF THE INVENTION

Figure 1:
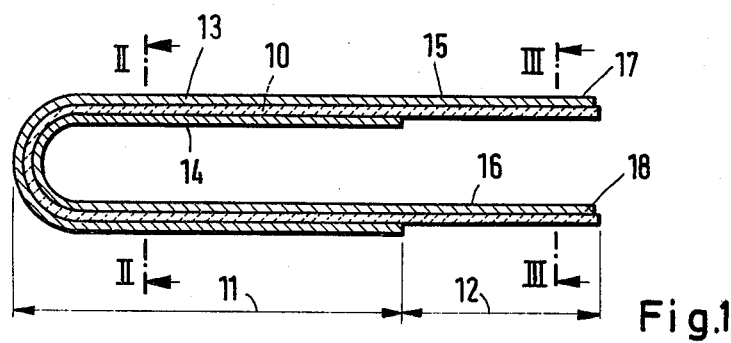
FIG. 1 shows an axial longitudinal cross section through a tubular probe, closed on one side, in accordance with the invention.
Figure 2:
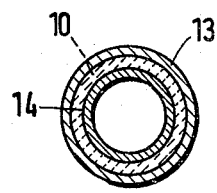
FIG. 2 is a cross section through the tubular probe along line II–II of FIG. 1.

The probe has at least one electrochemically active region provided with the electrodes and an electrochemically passive, or at least largely passive region which is provided with the contact points as well as with their electrical connections to the electrodes. The active region can therefore be chosen independently of the total length of the probe and be adapted specially for the intended application. Here, different temperatures of the passive part are without, or at least without appreciable effect on the voltage delivered by the probe.

A minimum of structural means is required if both regions of the probe have a solid electrolyte, on which the contact points as well as the connections are arranged with a large mutual distance for forming the passive region. Although in this embodiment, the contact points as well as the connections are arranged on the solid electrolyte, their effect as active electrodes is very small, as the path which is very long as compared to the active region, for the ions in the solid electrolyte of the passive region results in a high internal resistance and thus in a small delivered current, which hardly causes interference. The active region effects the voltage delivered by the probe. The passive region is without appreciable effect on the voltage delivered by the probe.

In order to reduce the influence of the passive part further, an insulating layer which does not conduct ions or electrons is inserted between the two regions. This eliminates particularly the effects of the junctions from the electrodes to the connections. The influence of the passive part on the measurement is practically completely eliminated by forming the passive region with an insulating part, preferably of ceramic, which does not conduct electrons or ions.

The connections consist advantageously of conductor runs. If the probe is of tubular design, it is advisable to arrange the conductor runs approximately diametrically. For a good compromise between the requirement of an active region as large as possible and the requirement of a measurement substantially unaffected by influence of temperature gradient and chemical reaction, it is advisable to have the passive region of the probe disposed in that part of the probe which is to extend in a probe housing.

In the drawings, identical parts in the individual figures have the same reference symbols.

Referring to FIG. 1, the probe comprises a solid-electrolyte tube 10 with a closed left and an open right end. Zirconium dioxide serves as the oxygen ion-conducting solid electrolyte. In the active region 11 of the probe which is provided for delivering the measurement signal and which extends from the tip of the solid-electrolyte tube 10 in the axial direction, the entire outer surface is preferably provided with an outer electrode 13 and the entire inside surface with an inner electrode 14. In some cases it may also be sufficient to make one or both electrodes as mutually opposite strips. The active region 11 is designed as to its electrode areas and the electrolyte thickness so that at the operating temperature a sufficiently low internal electric resistance is obtained, for instance, between 10 and 10,000 K$\Omega$, and preferably 10 to 100 K$\Omega$. The passive region 12 formed with the same solid electrolyte carries an outer connection 15 connected to the outer electrode 13 and an inner connection 16 connected to the inner electrode 14, the ends of which form the contact points 17 and 18.

Figure 3:
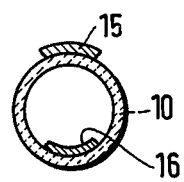
FIG. 3 is a cross section through the tubular probe along line III–III of FIG. 1.

The connections are electron-conducting and, as can be seen clearly from FIG. 3, consist of conductor runs, the width of which is between 1 and 10 mm., depending on the probe diameter, but preferably between 2 and 4 mm. It is important here that the path for the ions from the one to the other connection through the solid-electrolyte tube is very long, as thereby the internal electric resistance is increased considerably and the passive region 12 cannot therefore deliver an appreciably interfering current and thus, for all practical purposes, cannot falsify the measurement voltage. The connections 15 and 16 may be made of any electron-conducting, corrosion-resistant material but preferably, they consist of extensions of the respective electrodes. In order to ensure good contact with the potential leads which go on from there, the conductors can be widened at the contact points.

Figure 4:
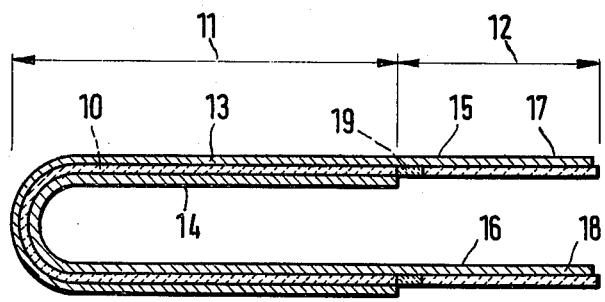
FIG. 4 is a variant of the tubular probe shown in FIG. 1.

The construction of the probe according to FIG. 4 is similar to that of the probe of FIG. 1. The difference between the probe of FIG. 1 and the probe of FIG. 4 consists merely in the solid electrolyte of the active region 11 being separated from the solid electrolyte of the passive region 12 by an interposed circular insulating layer 19 (FIG. 4). This measure creates a clean separation of the two regions.

The insulating layer consists preferably of gas-tight, sintered-glass ceramic which does not conduct ions or electrons, such as ceramic of the following composition: $SiO_2$, 35 to 50%; $MgO$, 50 to 30%; and $Al_2O_3$, 15 to 20%. The insulating layer is connected by a sintering or fusing process to the two parts of the tube, which, incidentally, may also have different outside diameters, as shown in FIG. 6.

Figure 5:
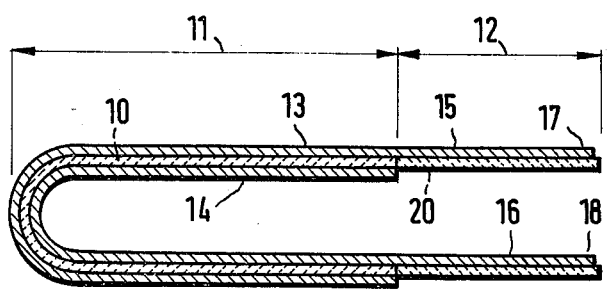
FIG. 5 is an axial longitudinal section of another variant of the tubular probe shown in FIG. 1.

The probe shown in FIG. 5 corresponds generally to the probe of FIG. 1. The difference between the probes is that the passive region 12 is built up on an insulating part of tubular shape 20 (FIG. 5) which is fastened to the solid-electrolyte tube 10, and the outside and inside diameter of the insulating part 20 corresponds approximately to the diameters of the solid-electrolyte tube 10. As this insulating part 20 consists of a material that does not conduct ions or electrons, there is practically no danger that the measurement result is influenced in any way by the passive region. This would not be the case if the connections 15 and 16 did not consist of narrow conductor runs but were simply formed by an extension of the electrodes 13 and 14 covering the entire inside and outside surfaces. The insulating part 20 preferably consists of magnesium silicate $Mg_2(SiO_4)$, magnesium-aluminum spinel $MgO.Al_2O_3$ or the sintered-glass ceramic mentioned above. The electrolyte tube is fastened to the insulating part either by directly sintering together the two parts or by inserting a connecting layer of glass solder or sintered-glass ceramic.

Figure 6:
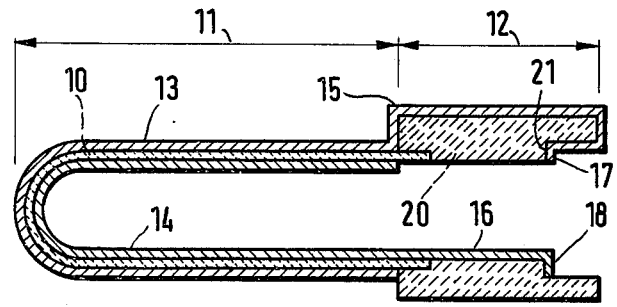
FIG. 6 is the tubular probe of FIG. 5 with another design of the insulating body.

The basic design of the probe shown in FIG. 6 corresponds to that of FIG. 5. However, the insulating part 20 of FIG. 6 is made in the shape of a circular flange, the outside diameter of which is larger than the corresponding diameter of the solid-electrolyte tube 10. In order to center this tube with respect to the flange, it is inserted into a step-like expansion of the flange opening and fastened there. The free end of the flange has likewise an inner step for forming the shoulder 21, on which the connections 15 and 16 end and form the contact points 17 and 18. To this end, the outer connection 15 is brought on the flange on the outside up to the shoulder 21, as can be seen in FIG. 6, and the inner connection 15 runs on the inner wall of the flange up to the shoulder 21. However, it would also be possible to also arrange the connection 15 on the inside wall of the flange approximately diametrically opposite to the connection 16 and to let it end on the shoulder 21. To this end it is necessary to bring the connection 15 at the joint of the tube and the flange from the outside to the inside, which can be done easily particularly if a connecting layer is interposed at this point. In order to avoid short circuits, the inner electrode 14 should not quite extend to the end of the solid-electrolyte tube 10 at this feedthrough point. The inside diameters of the solid-electrolyte tube and the flange are approximately equal and the ratio of the outside diameters is about 1 : 1.5 to 1 : 2. The choice of the material for the flange may be the same as those made in connection with FIG. 5.

For determining the size and length relations of the active to the passive region, the rule generally applies that the active region is made only large enough so that a sufficiently low internal resistance of the probe is provided. The remaining part of the probe is made passive. The size will vary depending on the given measurement problem. As a minimum, however, at least the region of the probe which is intended to be inserted in a probe housing, should be designed as passive.

There are claimed:

1. In a probe for an electrochemical oxygen measurement pickup having an oxygen ion-conducting solid electrolyte with electrodes and electrical contact points connected to the electrodes, the combination therewith of an electrochemically active region of the probe which has the electrodes and the oxygen ion-conducting solid electroltye for passage of oxygen ions through the solid electrolyte, and an electrochemically passive region of the probe which carries the contact points as well as their electrical connections to the electrodes, and wherein the passive region has a solid electrolyte on which the contact points and electrical connections are arranged, with the contact points spaced from each other as well as the electrical connections to the electrodes spaced from each other to require ions moving from one contact point to another and one connection to another to travel a long path, thereby reducing an interfering current, and wherein the active and passive regions are separated by an insulating layer which does not conduct ions or electrons.

2. Probe according to claim 1, wherein the insulating layer consists substantially of magnesium silicate $Mg_2(SiO_4)$, magnesium-aluminum spinel $MgO.Al_2O_3$ or sintered glass ceramic with approximately the composition: $SiO_2$, 35 to 50%; MgO, 50 to 30%; and $Al_2O_3$, 15 to 20%.

3. In a probe for an electrochemical oxygen measurement pickup having an oxygen ion-conducting solid electrolyte with electrodes and electrical contact points connected to the electrodes, the combination therewith of an electrochemically active region of the probe of tubular shape which has the electrodes and the oxygen ion-conducting solid electroylyte for passage of oxygen ions through the solid electrolyte, and a passive region of the probe of tubular shape which carries the contact points as well as their electrical connections to the electrodes, with the passive region formed with an insulating part which does not conduct electrons or ions and with said passive region extending up to and directly fastened to said solid electrolyte.

4. Probe according to claim 3, wherein the insulating part consists substantially of magnesium silicate $Mg_2(SiO_4)$, magnesium-aluminum spinel $MgO.Al_2O_3$ or sintered glass ceramic with approximately the composition: $SiO_2$, 35 to 50%; MgO, 50 to 30%, and $Al_2O_3$, 15 to 20%.

5. In a probe for an electrochemical oxygen measurement pickup having an oxygen ion-conducting solid electrolyte with electrodes and electrical contact points connected to the electrodes, the combination therewith of a tubular-shaped probe having an electrochemically active region of the probe which has the electrodes and the oxygen ion-conducting solid electrolyte for passage of oxygen ions through the solid electrolyte, and an electrochemically passive region of the probe which carries the contacts points as well as their electrical connections to the electrodes, with the passive region having a solid electrolyte on which the contact points and electrical connections are arranged, and with the contact points spaced from each other as well as the electrical connections consisting of conductor runs to the electrodes spaced from each other, with the conductor runs arranged diametrically opposite to each other on the tubular probe to require ions moving from one contact point to another and one connection to another to travel a long path thereby reducing an interfering current.

* * * * *